(12) United States Patent
Tatsumoto et al.

(10) Patent No.: US 6,537,431 B1
(45) Date of Patent: Mar. 25, 2003

(54) CERAMIC LAMINATE BODY OF A GAS SENSOR

(75) Inventors: Hirohiko Tatsumoto, Kariya (JP); Shoichiro Emmei, Nagoya (JP)

(73) Assignee: Denso Corporation, Aichi-Pref. (JP)

( * ) Notice: Subject to any disclaimer, the term of this patent is extended or adjusted under 35 U.S.C. 154(b) by 0 days.

(21) Appl. No.: 09/572,775

(22) Filed: May 17, 2000

(30) Foreign Application Priority Data

May 17, 1999 (JP) .............................. 11-135459
Apr. 5, 2000 (JP) ....................... 2000-103854

(51) Int. Cl.$^7$ ............................................ G01N 27/407
(52) U.S. Cl. ................... 204/426; 204/421; 204/424
(58) Field of Search .................................. 204/421–429

(56) References Cited

U.S. PATENT DOCUMENTS 4,450,065 A * 5/1984 Yamada et al.

FOREIGN PATENT DOCUMENTS

| JP | 59-29107 | 2/1984 |
| JP | 9-304321 | 11/1997 |

* cited by examiner

*Primary Examiner*—T. Tung
(74) *Attorney, Agent, or Firm*—Nixon & Vanderhye PC (57) ABSTRACT

A first ceramic sheet and a second ceramic sheet are bonded via an adhesive layer so as to form a closed hollow space between them. A tapered portion with a slant surface is formed at an inner end of the adhesive layer so as to protrude into the closed hollow space. The thickness t1 of the adhesive layer is equal to or smaller than 40 $\mu$m, and the protruding length L1 of the tapered portion is equal to or larger than 2.5 t1.

9 Claims, 7 Drawing Sheets

CERAMIC LAMINATE BODY OF A GAS SENSOR

BACKGROUND OF THE INVENTION

The present invention relates to a ceramic laminate body preferably applied to various gas sensors which are configured into a laminated or multilayered structure.

According to a conventional method, a ceramic laminate body with a closed hollow space therein is manufactured in the following manner.

Two similar ceramic green sheets (referred to first ceramic green sheets) and one other ceramic green sheet (referred to second ceramic green sheet) are prepared. The second ceramic green sheet and the first ceramic green sheets are substantially identical in their dimensions. The second ceramic green sheet has a window at a central region thereof. This window serves as a closed hollow space after an assembling operation of ceramic green sheets according to which the second ceramic green sheet is laminated between two first ceramic green sheets.

A slurry, forming a green adhesive layer, is applied on a peripheral region of each of the first ceramic green sheets. Then, the second ceramic green sheet is laminated between the first ceramic green sheets to bond them via the green adhesive layer, thereby forming a green laminate body with a closed hollow space therein.

Next, the green laminate body is degreased and sintered.

Figure 12:
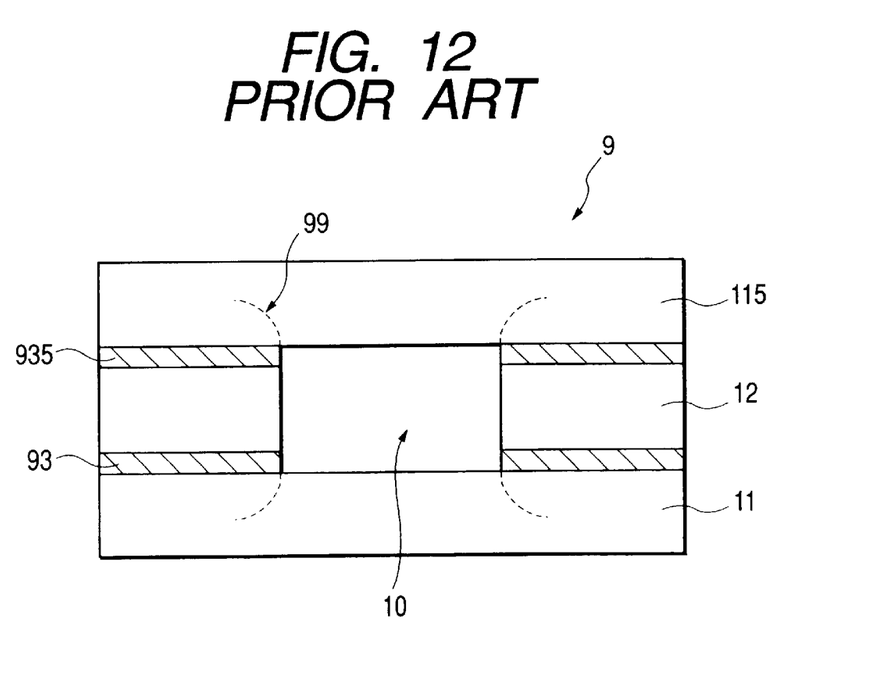
FIG. 12 is a cross-sectional view showing a conventional ceramic laminate body.

FIG. 12 shows a conventional ceramic laminate body 9 thus formed, according to which two first ceramic sheets 11 and 115 are bonded to the second ceramic sheet 12 via adhesive layers 93 and 935 so as to form a closed hollow space 10 between them (refer to the unexamined Japanese patent publication No. 59-29107).

However, the green adhesive slurry contains a great amount of organic binder compared with those involved in the first and second ceramic green sheets. In general, the organic binder is necessary to enhance the bonding or adhesive force.

Due to the presence of this organic binder, the green adhesive layer has a relatively low density in the initial condition. When the green adhesive layer is subjected to the degreasing and sintering processes, the adhesive layer contracts greatly.

The contraction of the adhesive layers possibly causes peeling of the ceramic sheets or generates voids. FIG. 12 shows cracks 99 appearing in the vicinity of the adhesive layers, which are caused by the contraction difference between the adhesive layers and the ceramic sheets.

SUMMARY OF THE INVENTION

An object of the present invention is to provide a ceramic laminate body which is free from cracks or any peeling-off phenomenon derived from a thermal contraction difference between adhesive layers and ceramic sheets.

Another object of the present invention is to provide a method for manufacturing this ceramic body.

Still another object of the present invention is to provide an application of this ceramic laminate body to a gas sensor.

In order to accomplish these and other related objects, the present invention provides a first ceramic laminate body comprising a first ceramic sheet and a second ceramic sheet which are bonded via an adhesive layer so as to form a closed hollow space between the first ceramic sheet and the second ceramic sheet. A tapered portion with a slant surface is formed at an inner end of the adhesive layer so as to protrude into the closed hollow space. A thickness t1 of the adhesive layer is equal to or smaller than 40 $\mu$m, and a protruding length L1 of the tapered portion is equal to or larger than 2.5 t1.

Preferably, the thickness t1 of the adhesive layer is in a range from 20 $\mu$m to 40 $\mu$m.

Furthermore, the present invention provides a second ceramic laminate body comprising a first ceramic sheet and a second ceramic sheet which are bonded via an adhesive layer so as to form a closed hollow space between the first ceramic sheet and the second ceramic sheet, wherein a tapered portion with a slant surface is formed at an inner end of the adhesive layer so as to retract at least partly in a gap for the adhesive layer formed between the first and second ceramic sheets. A thickness t1 of the adhesive layer is within a range from 10 $\mu$m to 40 $\mu$m. An extended length L13 of the tapered portion is equal to or larger than 2.5 t1. And, the following relationship is established:

$$0 < L12 < 0.5\ L11$$

where L11 represents an overall longitudinal length of the adhesive layer, and L12 is a retraction length of the tapered portion.

Furthermore, the present invention provides a first gas sensing element comprising a sensor section for measuring a gas concentration of a measured gas, and a support for supporting the sensor section. The sensor section comprises a solid electrolytic layer, and a pair of electrodes formed on opposite surfaces of the solid electrolytic layer. The support has a recessed portion defining a closed hollow space when the support is assembled with the sensor section. An adhesive layer is interposed between the sensor section and the support to bond a surface of the solid electrolytic layer to a surface of the support so that the closed hollow space is formed between the solid electrolytic layer and the support. A tapered portion with a slant surface is formed at an inner end of the adhesive layer so as to protrude into the closed hollow space. A thickness t1 of the adhesive layer is equal to or smaller than 40 $\mu$m, and a protruding length L1 of the tapered portion is equal to or larger than 2.5 t1.

Furthermore, the present invention provides a second gas sensing element comprising a sensor section for measuring a gas concentration of a measured gas, and a support for supporting the sensor section. The sensor section comprises a solid electrolytic layer, and a pair of electrodes formed on opposite surfaces of the solid electrolytic layer. The support has a recessed portion defining a closed hollow space when the support is assembled with the sensor section. An adhesive layer is interposed between the sensor section and the support to bond a surface of the solid electrolytic layer to a surface of the support so that the closed hollow space is formed between the solid electrolytic layer and the support. A tapered portion with a slant surface is formed at an inner end of the adhesive layer so as to retract at least partly in a gap for the adhesive layer formed between the sensor section and the support. The thickness t1 of the adhesive layer is within a range from 10 $\mu$m to 40 $\mu$m. An extended length L13 of the tapered portion is equal to or larger than 2.5 t1, and the following relationship is established:

$$0 < L12 < 0.5\ L11$$

where L11 represents an overall longitudinal length of the adhesive layer, and L12 is a retraction length of the tapered portion.

Moreover, the present invention provides a first method for manufacturing a ceramic laminate body, comprising the steps of forming a green laminate body by laminating a first ceramic green sheet and a second ceramic green sheet via a green adhesive layer so as to form a closed hollow space between the first and second ceramic green sheets, and sintering the green laminate body, wherein a tapered portion with a slant surface is formed at an inner end of the green adhesive layer so as to protrude into the closed hollow space, a thickness t0 of the green adhesive layer is within a range from 40 $\mu$m to 80 $\mu$m, and a protruding length L0 of the tapered portion is equal to or larger than 2 t0.

The present invention provides a second method for manufacturing a ceramic laminate body, comprising the steps of forming a green laminate body by laminating a first ceramic green sheet and a second ceramic green sheet which are bonded via a green adhesive layer so as to form a closed hollow space between the first and second ceramic green sheets, and sintering the green laminate body, wherein a tapered portion with a slant surface is formed at an inner end of the green adhesive layer so as to retract at least partly in a gap for the green adhesive layer formed between the first and second ceramic green sheets, a thickness t0 of the green adhesive layer is within a range from 20 $\mu$m to 80 $\mu$m, an extended length L03 of the tapered portion is equal to or larger than 2 t0, and the following relationship is established:

$$0 < L02 < 0.5 \ L01$$

where L01 represents an overall longitudinal length of the green adhesive layer, and L02 is a retraction length of the tapered portion.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Preferred embodiments of the present invention will be explained hereinafter with reference to attached drawings.

First Embodiment

Figure 1A:
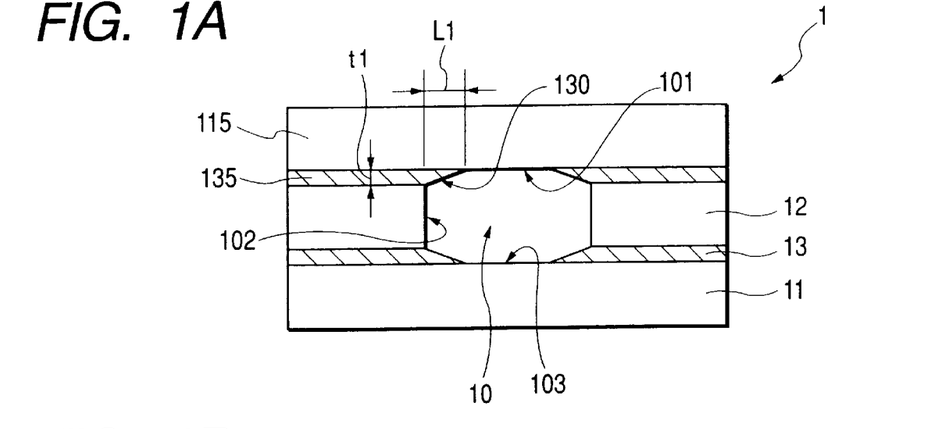
FIG. 1A is a cross-sectional view showing a ceramic laminate body in accordance with a first embodiment of the present invention.
Figure 1B:
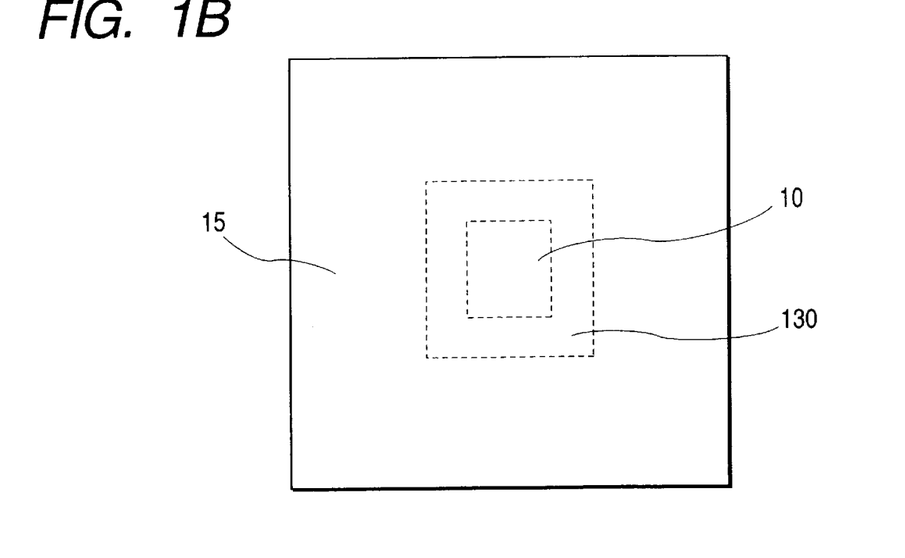
FIG. 1B is a plan view showing the ceramic laminate body in accordance with the first embodiment of the present invention.
Figure 1C:
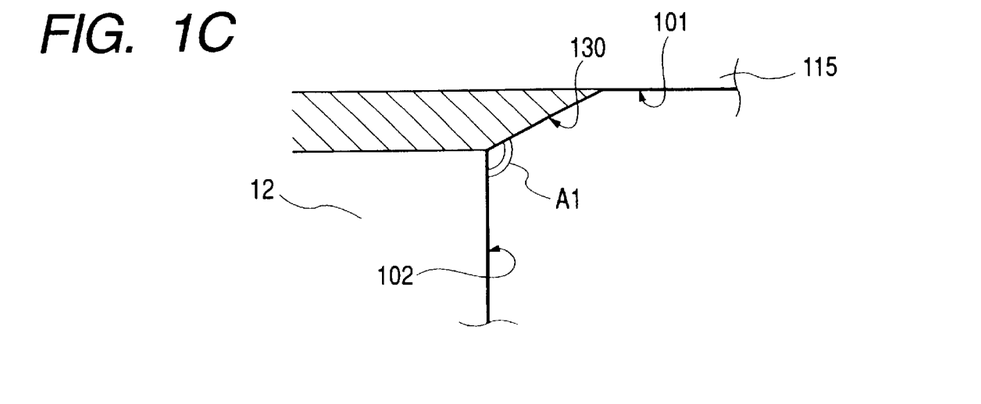
FIG. 1C is an enlarged cross-sectional view showing a tapered portion of an adhesive layer in accordance with the first embodiment of the present invention.

FIGS. 1A to 1C show a ceramic laminate body 1 of the first embodiment, according to which a lower ceramic sheet 11 (serving as a first ceramic sheet) is bonded to a lower surface of an intermediate ceramic sheet 12 (serving as a second ceramic sheet) via an adhesive layer 13 and an upper ceramic sheet 115 (serving as another first ceramic sheet) is bonded to an upper surface of the intermediate ceramic sheet 12 via an adhesive layer 135. A closed hollow space 10, surrounded by the upper and lower ceramic sheets 11, 115 and the intermediate ceramic sheet 12, is formed in the ceramic laminate body 1.

A tapered portion 130 with a slant surface, formed at an inner end of each of the adhesive layers 13 and 135, protrudes into the hollow space 10 from an inner end of the intermediate ceramic sheet 12. The inner end of the intermediate ceramic sheet 12 serves as a side wall 102 of the closed hollow space 10. A protruding length L1 of the tapered portion 130 is defined as an overhang from the side wall 102 of the closed hollow space 10 as shown in FIG. 1A.

As enlargedly shown in FIG. 1C, a proximal end of the tapered portion 130 (i.e., a starting point of the slant surface) is positioned just on the corner edge of the intermediate ceramic sheet 12 where the upper (or lower) surface of intermediate ceramic sheet 12 meets with the side wall 102 of the hollow space 10. A distal end of the tapered portion 130 (i.e., an ending point of the slant surface) merges into the inside surface of the lower ceramic sheet 11 or into the upper ceramic sheet 115. The inside surface (i.e., an upper surface) of the lower ceramic sheet 11 serves as a bottom 103 of the closed hollow space 10. The inside surface (i.e., a lower surface) of the upper ceramic sheet 115 serves as a ceiling 101 of the closed hollow space 10.

The lower ceramic sheet 11 (i.e., first ceramic sheet) is made of alumina. The intermediate ceramic sheet 12 (i.e., second ceramic sheet) is made of alumina. The upper ceramic sheet 115 (i.e., first ceramic sheet) is made of zirconia. The intermediate ceramic sheet 12 is laminated on the lower ceramic sheet 11 via the adhesive layer 13 and the upper ceramic sheet 115 is laminated on the intermediate ceramic sheet 12 via the adhesive layer 135 so as to form a laminate structure (or a multilayered structure) with the closed hollow space 10 as shown in FIG. 1A.

As shown in FIG. 1B, the closed hollow space 10 has a rectangular shape when seen from the top or the bottom.

Accordingly, the tapered portion 130 is formed along all of four peripheral-sides of the rectangular hollow space.

The ceramic laminate body of the first embodiment is manufactured in the following manner.

First, a first ceramic green sheet 215 for the ceramic sheet 115 is formed in the following manner.

Prepared materials for the first ceramic green sheet 215 are as follows:

- 71.7 wt % zirconia power having a mean grain size of 0.6 μm with additives of yttria;
- 2.5 wt % polyvinyl butyral serving as an organic binder;
- 5.9 wt % plastic dibutyl phthalate;
- 0.7 wt % dispersion-type sorbitan triolate; and
- 19.2 wt % solvent mixture of ethanol and toluene for solving and dispersing the above materials to form a slurry.

From this slurry, a sheet body having a thickness of approximately 300 μm is obtained by using the doctor blade method.

Then, the obtained sheet body is cut into a predetermined rectangular shape for the first ceramic green sheet 215.

Next, first and second ceramic green sheets 21 and 22 for the ceramic sheets 11 and 12 are formed in the following manner.

Prepared materials for the first and second ceramic green sheets 21 and 22 are as follows:

- 53.2 wt % alumina power having a mean grain size of 0.3 μm;
- 3.8 wt % polyvinyl butyral serving as an organic binder; and
- 34 wt % solvent mixture of ethanol and toluene for solving and dispersing the above materials to form a slurry.

From this slurry, two sheet bodies having a thickness of approximately 300 μm are obtained by using the doctor blade method.

Then, one of the obtained sheet bodies is cut into a predetermined rectangular shape for the first ceramic green sheet 21.

The other of the obtained sheet bodies is cut into a predetermined rectangular shape with a rectangular window for the second ceramic green sheet 22. The rectangular window serves as the closed hollow space 10.

Next, an adhesive material for a green adhesive layer 23 will be explained. The green adhesive layer 23 becomes the adhesive layer 13.

Prepared materials for the green adhesive layer 23 are as follows:

- 44.4 wt % alumina powder having a mean grain size of 0.3 μm;
- 19.2 wt % alkyl ester polymethacrylate serving as an organic binder;
- 2.8 wt % dispersion-type polycarboxylic acid; and
- 33.4 wt % organic solvent mixture of ethanol and terpineol for solving and dispersing the above materials to form a paste.

From this paste, the adhesive material is formed by using a three roll mill.

Next, the formation of a green laminate body will be explained.

Figure 2A:
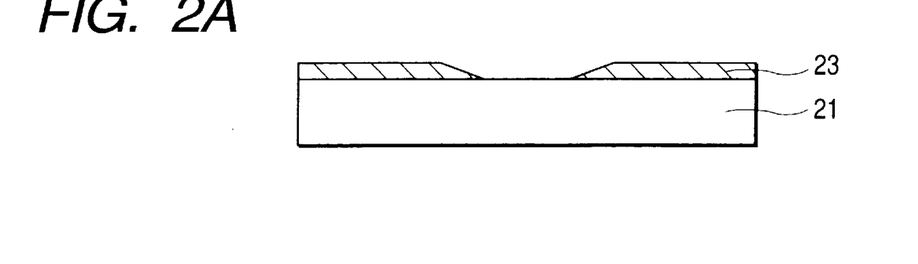
FIGS. 2A to 2C are views explaining the manufacturing processes of the ceramic laminate body in accordance with the first embodiment of the present invention.
Figure 3:
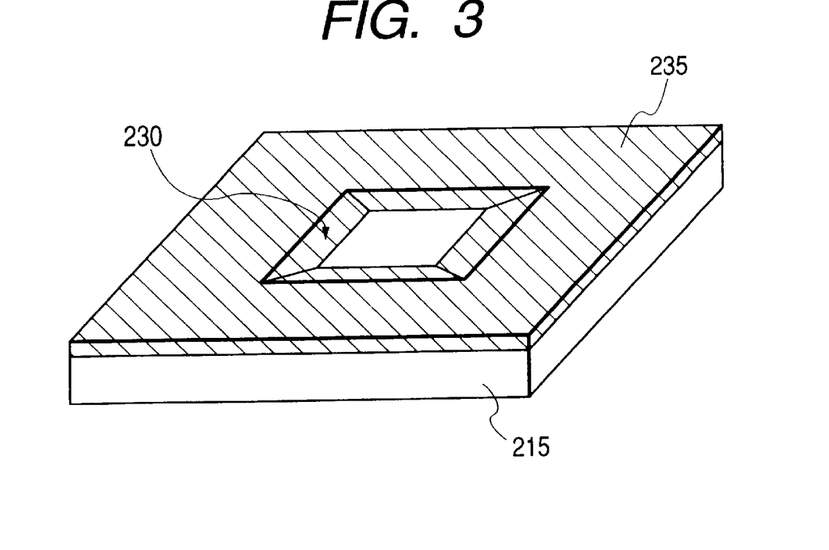
FIG. 3 is a perspective view showing a green adhesive layer applied on a ceramic sheet and the tapered portion in accordance with the first embodiment of the present invention.

As shown in FIG. 2A and in FIG. 3, the adhesive material is applied on the first ceramic green sheet 215 (made of zirconia) by using the screen printing method, to obtain a green adhesive layer 235. In this case, because of surface tension, the green adhesive layer 235 expands naturally along its back side brought into contact with the first ceramic green sheet 215. Thus, a tapered portion 230 is formed at the inner peripheral edge of the green adhesive layer 235.

Similarly, the adhesive material is applied on the first ceramic green sheet 21 (made of alumina) by using the screen printing method, to obtain a green adhesive layer 23. Because of surface tension, the green adhesive layer 23 expands naturally along its back side brought into contact with the first ceramic green sheet 21. Thus, a tapered portion 230 is formed at the inner peripheral edge of the green adhesive layer 23.

Figure 2B:
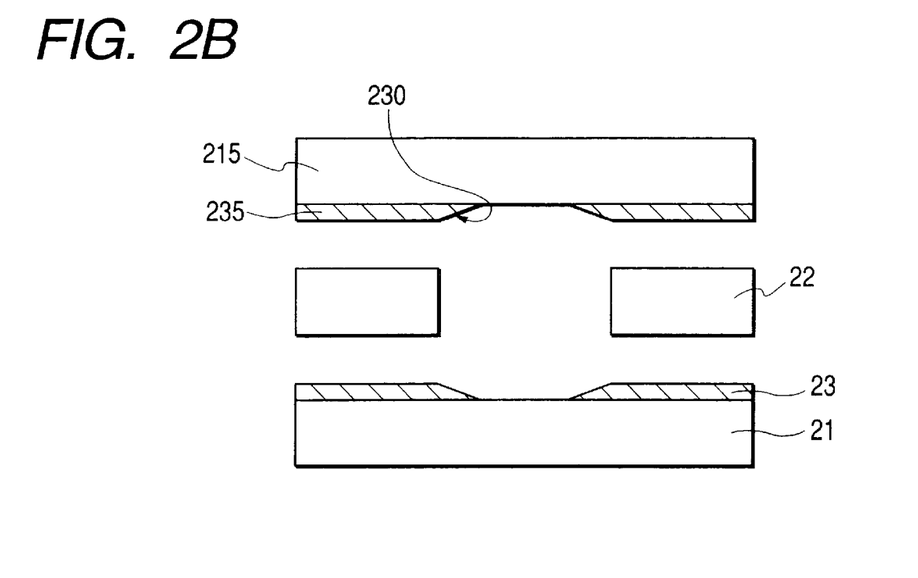
Figure 2C:
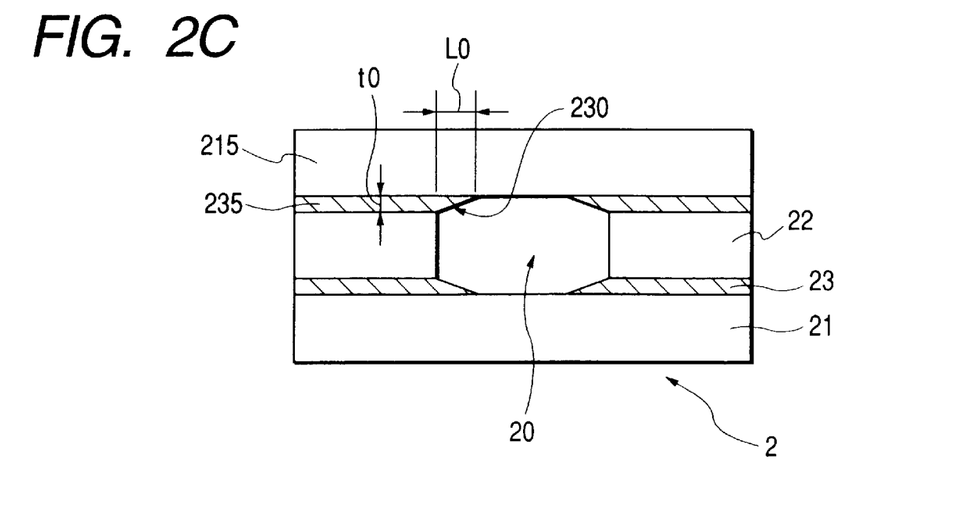

Next, as shown in FIG. 2B, the first ceramic green sheets 21 and 215 and the second ceramic green sheet 22 are laminated and pressed under the pressure of 0.3 MPa to bond them integrally. Thus, a green laminate body 2 with a closed hollow space 20 therein is obtained as shown in FIG. 2C.

L0 represents a protruding length of the green adhesive layer 23 (or 235), and t0 represents a thickness of the green adhesive layer 23 (or 235). The protruding length L0 is an overhang of the tapered portion 230 from the side wall of the closed hollow space 20. Preferably, L0 is approximately 200 μm and t0 is approximately 50 μm.

The green laminate body 2 is heated up to the maximum temperature of 1,450° C. and sintered under such a higher temperature condition.

Though this sintering operation, the green laminate body 2 becomes the ceramic laminate body 1 shown in FIG. 1. The size of the adhesive layer 13 (or 135) is L1=160 μm and t1=25 μm. In other words, the adhesive layer is subjected to substantial shrinkage equivalent to L0−L1=40 μm and t0−t1=25 μm occurring during the sintering operation.

Table 1 shows the result of the test conducted to evaluate the properties of the ceramic laminate body. In this evaluation test, several samples (No. 1 to No. 6) were prepared as the green laminate bodies which are different in the thickness t0 and the overhang L0 of the green adhesive layer. Every sample of the green laminate body was sintered to obtain the ceramic laminate body with the thickness t1. The condition of each sample of the green laminate body was checked by observer's eyes on a cut model of each obtained ceramic laminate body which is cut in the vicinity of the hollow space.

In this test, a total of ten ceramic laminate bodies were prepared for each sample.

TABLE 1

| sample no. | 1 | 2 | 3 | 4 | 5 | 6 |
|---|---|---|---|---|---|---|
| t0 (μm) | t0 < 40 | t0 < 40 | 40 ≦ t0 ≦ 80 | 40 ≦ t0 ≦ 80 | 80 < t0 | 80 < t0 |
| t1 (μm) | t1 < 20 | t1 < 20 | 20 ≦ t1 ≦ 40 | 20 ≦ t1 ≦ 40 | 40 < t1 | 40 < t1 |
| L0 (μm) | L0 < 2t0 | 2t0 ≦ L0 | L0 < 2t0 | 2t0 ≦ L0 | L0 < 2t0 | 2t0 ≦ L0 |
| sintered | voids & | voids | cracks | no voids & | cracks | cracks |

TABLE 1-continued

| sample no. | 1 | 2 | 3 | 4 | 5 | 6 |
|---|---|---|---|---|---|---|
| condition | cracks (1/10) | | (2/10) | no cracks | (8/10) | (3/10) |
| judgement | X | Δ | X | ○ | X | X |

The sample 1 is a ceramic laminate body which satisfies the dimensional conditions of t0<40 μm, t1<20 μm, and L0<2t0.

As shown in Table 1, the sample 1 has caused voids among the first ceramic sheet, the second ceramic sheet, and the adhesive layers during the sintering operation. Furthermore, cracks were found in one of ten tested ceramic laminate bodies of the sample 1 (as indicated by 1/10 in Table 1). The generated voids induce the peeling-off phenomenon between the ceramic sheet and the adhesive layer. Thus, the bonding strength of the adhesive layer is weakened greatly.

As understood from Table 1, only the sample 4 has demonstrated excellent properties.

Regarding the sample 2, the judgement result becomes Δ because of generation of voids only. If the sample 2 is used as a gas sensing element (refer to the later-described second embodiment), it will be difficult to maintain the airtightness of the closed hollow space at a satisfactory level as well as to assure a sufficient mechanical strength.

Next, the functions and effects of the first embodiment will be explained.

According to the ceramic laminate body of the first embodiment, the tapered portion 130 with a slant surface is formed at an inner end of the adhesive layer 13 (and 135) so as to protrude into the closed hollow space 10. In other words, the tapered portion 130 overhangs inward (i.e., toward the closed hollow space 10) from the adhesive layer 13 (and 135). The thickness t1 of the adhesive layer 13 (and 135) is within a range from 20 μm to 40 μm. The protruding length (i.e., an overhang) L1 of the tapered portion 130 is equal to or larger than 2.5 t1.

In the condition of the green laminate body 2, the thickness t0 of the green adhesive layer 23 (and 235) is within a range from 40 μm to 80 μm. The protruding length (i.e., overhang) L0 of the tapered portion 230 is equal to or larger than 2 t0.

In general, the green adhesive layer 23 (and 235) shrinks during the manufacturing processes of the ceramic laminate body 1. However, the arrangement of the first embodiment can suppress the tensile stress acting among the first and second ceramic green sheets 21, 215, and 22. This is effective to eliminate the peeling-off phenomenon of the ceramic sheets and also to suppress the generation of cracks (refer to 99 shown in FIG. 12).

Accordingly, the first embodiment of the present invention provides a ceramic laminate body which is free from the cracks or the peeling-off phenomenon derived from the thermal contraction difference between the adhesive layers and the ceramic sheets.

Second Embodiment

A gas sensing element of a second embodiment will be explained with reference to FIGS. 4 to 6.

A gas sensing element 3 roughly consists of a sensor section 39, a support 35, and a heater section 38.

The sensor section 39 measures a gas concentration of an ambient gas (hereinafter, referred to as "measured gas") surrounding the gas sensing element 3. The sensor section 39 comprises a solid electrolytic layer 33 (i.e., first ceramic sheet), a pair of electrodes 311 and 312 formed on opposite surfaces of the solid electrolytic layer 33, and a protective layer 31 covering the electrodes 311 and 312 against the measured gas. The protective layer 31 and the solid electrolytic layer 33 are bonded via the adhesive layer 32.

The support 35 (i.e., second ceramic sheet) has the closed hollow space 30 serving as an air introducing passage. This hollow space 30 is opened to the air at the base terminal of the gas sensing element 3 and is closed at its front end where the electrodes 311 and 312 are provided (refer to FIG. 4).

Figure 5:
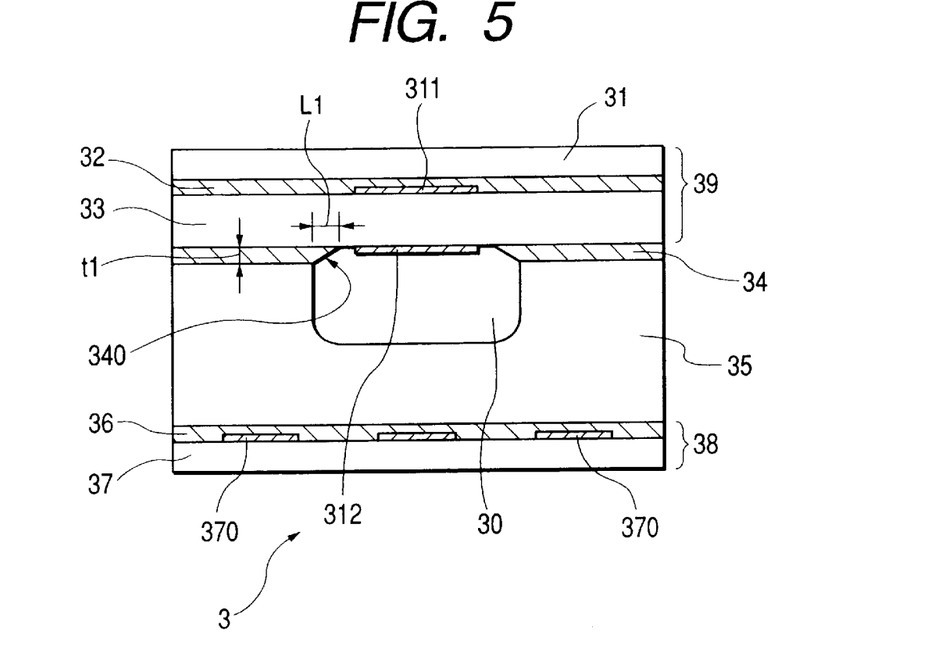
FIG. 5 is a cross-sectional view showing a gas sensing element in accordance with the second embodiment of the present invention.

As shown in FIG. 5, in the sensor section 39, the protective layer 31 is bonded to the upper surface of the solid electrolytic layer 33 via the adhesive layer 32. The upper electrode 311 is mounted on the upper surface of the solid electrolytic layer 33 and embedded in the adhesive layer 32. The support 35 is bonded to the lower surface of the solid electrolytic layer 33 via the adhesive layer 34. The lower electrode 311 is attached to a central region of the lower surface of the solid electrolytic layer 33 where the adhesive layer 34 is not provided.

Figure 4:
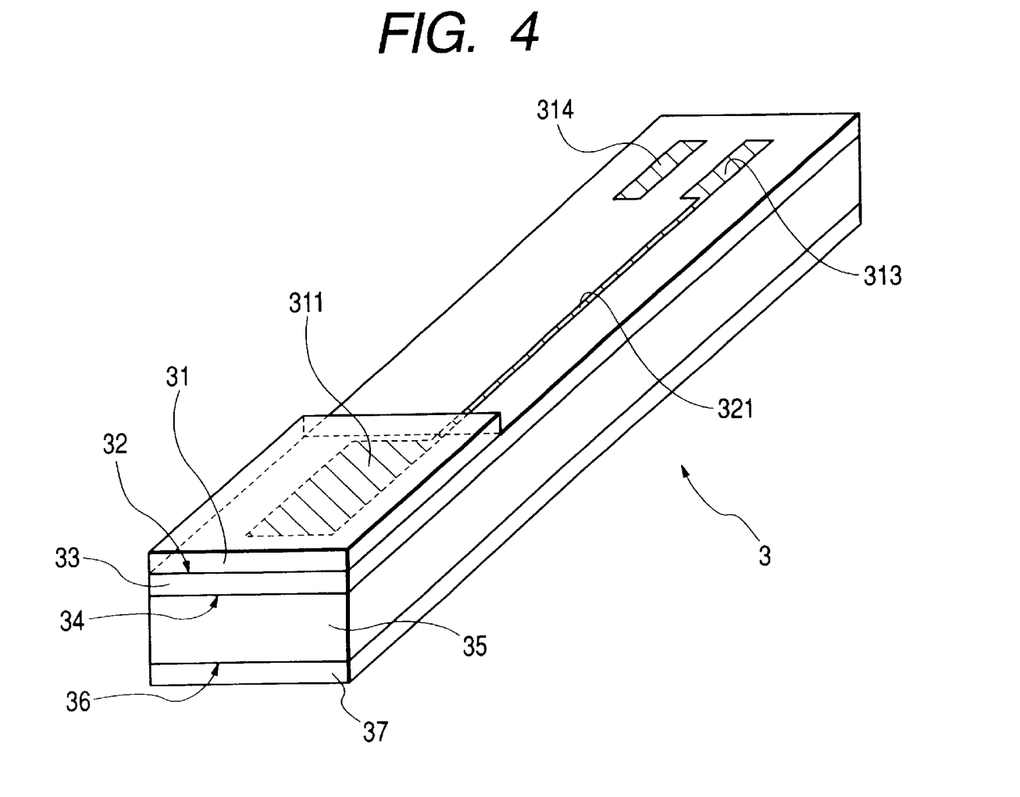
FIG. 4 is a perspective view showing a gas sensing element in accordance with a second embodiment of the present invention.

As shown in FIG. 4, the upper electrode 311 is connected to a terminal 313 via a lead 321. The lower electrode 312 is connected to a terminal 314 via a lead (not shown). The terminals 313 and 314 are positioned at the base end of the gas sensing element 3 and are directly attached to the upper surface of the solid electrolytic layer 33. The output signal of the gas sensor section 39, representing the gas concentration of the measured gas, is taken out through the terminals 313 and 314.

The closed hollow space 30 is defined by the solid electrolytic layer 33 and the support 35 which are bonded by the adhesive layer 34. A tapered portion 340 with a slant surface is formed at an inner end of the adhesive layer 34 so as to protrude into the closed hollow space 30 with an overhang L1.

Figure 6:
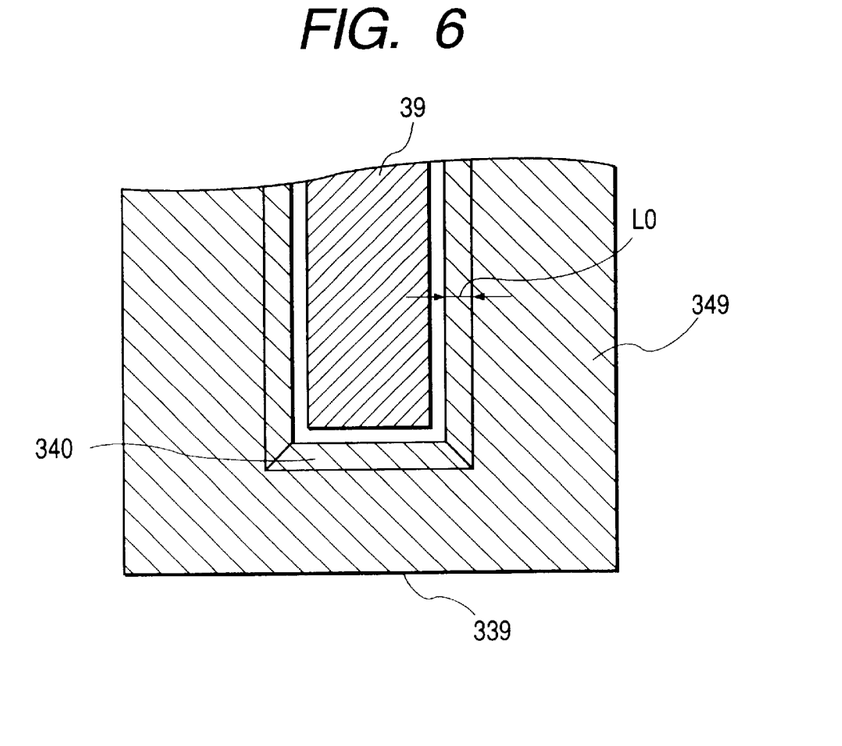
FIG. 6 is a view showing a solid electrolytic green sheet, a green adhesive layer, and an electrode print portion in accordance with the second embodiment of the present invention.

As shown in FIG. 6, the tapered portion 340 is formed along all of four peripheral sides of the rectangular hollow space 30. The thickness t1 of the adhesive layer 34 is 30 μm (i.e., t1=30 μm). The overhang L1 of the tapered portion 340 is 100 μm (i.e., L1=100 μm).

The heater section 38 comprises a heating element 370 attached on a heater substrate 37 which is bonded to the lower surface of the support 35 via an adhesive layer 36. The heating element 370 is embedded in the adhesive layer 36.

The above-described gas sensing element 3 is manufactured in the following manner.

First, a zirconia green sheet for the solid electrolytic layer 33 is formed by mixing the following materials:
  zirconia powder having a mean grain size of 0.6 μm with additives of yttria;
  methyl cellulose serving as an organic binder; and
  water as a solvent.

The mixture of the above materials is kneaded into a pellet by using an appropriate kneader. Then, the obtained pellet is shaped into a green sheet having a thickness of 300 µm by using an appropriate extruder.

Then, the obtained green sheet is configured into a predetermined shape by punching. Then, the printing patterns for the electrodes 311 and 312 are formed on the opposite surfaces of the green sheet by applying a Pt paste on each surface by using the screen printing method.

Next, an alumina green sheet for the support 35 and the heater substrate 37 is formed by mixing the following materials:

alumina powder having a mean grain size of 0.3 µm;

methyl cellulose serving as an organic binder; and water as a solvent.

The mixture of the above materials is kneaded into a pellet by using an appropriate kneader. Then, by using an appropriate extruder, the obtained pellet is shaped into a green sheet having a thickness of 1,000 µm and also into another green sheet having a thickness of 300 µm.

The obtained green sheet (of 1,000 µm) for the support 35 is configured into a predetermined shape by punching, so as to form a groove serving as the closed follow space 30.

Furthermore, the obtained green sheet (of 300 µm) for the heater substrate 37 is configured into a predetermined shape by punching. Then, the printing pattern for the heating element 370 is formed on the surface of the green sheet by applying a Pt paste on the surface by using the screen printing method.

Next, an alumina green sheet for the protective layer 31 is formed by mixing the following materials:

alumina powder having a mean grain size of 0.6 µm;

methyl cellulose serving as an organic binder; and water as a solvent.

The mixture of the above materials is kneaded into a pellet by using an appropriate kneader. Then, the obtained pellet is shaped into a green sheet having a thickness of 200 µm by using an appropriate extruder.

Then, the obtained green sheet is configured into a predetermined shape by punching, thereby obtaining the green sheet for the protective layer 31.

Next, an adhesive material for the adhesive layers 34 and 36 is formed by mixing the following materials:

44.4 wt % alumina powder having a mean grain size of 0.3 µm;

19.2 wt % alkyl ester polymethacrylate serving as an organic binder;

2.8 wt % dispersion-type polycarboxylic acid; and 33.4 wt % organic solvent mixture of ethanol and terpineol for solving and dispersing the above materials.

The above materials are kneaded by using a three roll mill to obtain a paste of the adhesive material.

The obtained paste of the adhesive material is applied on the green sheet for the solid electrolytic layer 33 and the green sheet for the heater substrate 37 by screen printing. The adhesive material for the heater substrate 37 is applied entirely on the surface of the green sheet.

As shown in Fig, 6, a green adhesive layer 349 (i.e., the adhesive material) is provided on the surface of the green sheet 339 for the solid electrolytic layer 33 except for the region facing to the groove of the support 35 as well as the region for a print pattern for the electrode 312. In this case, because of surface tension, the green adhesive layer 349 (i.e., the adhesive material) expands naturally along its back side brought into contact with the solid electrolytic layer 33. Thus, the tapered portion 340 is formed at the inner peripheral edge of the green adhesive layer 349. In this embodiment, the protruding length (i.e., overhang) L0 of the tapered portion 340 is 150 µm in the green condition. The thickness t0 of the green adhesive layer 349 is 60 µm.

Next, the an adhesive material for the adhesive layer 32 is formed by mixing the following materials:

41.6 wt % alumina powder having a mean grain size of 0.5 µm;

22.4 wt % alkyl ester polymethacrylate serving as an organic binder;

2.6 wt % dispersion-type polycarboxylic acid; and 33.4 wt % organic solvent mixture of ethanol and terpineol for solving and dispersing the above materials.

The above materials are kneaded by using a three roll mill to obtain a paste of the adhesive material.

When sintered, the adhesive layer 32 becomes porous. Thus, the measured gas can penetrate the adhesive layer 32 to reach the electrode 311.

The obtained paste of the adhesive material is applied on the entire surface of the green sheet for the protective layer 31 by screen printing, thereby forming a green adhesive layer.

Subsequently, the four green sheets for the protective layer 31, the solid electrolytic layer 33, the support 35, and the heater substrate 37 are laminated (or stacked) in this order via the green adhesive layers as shown in FIG. 5. Then, the obtained laminated assembly is pressed under the pressure of 0.3 MPa to obtain a green laminate body.

Thereafter, the obtained green laminate body is heated up to the maximum temperature of 1,450° C. Thus, the gas sensing element 3 shown in FIG. 4 is obtained.

According to the properties test of the gas sensing element 33 thus manufactured, no peeling-off phenomenon was found in any of the protective layer 31, the solid electrolytic layer 33, the support 35, and the heater substrate 37. Furthermore, no cracks were found in the closed hollow space 30.

According to the gas sensing element of the second embodiment, the tapered portion 340 with a slant surface is formed at the inner end of the adhesive layer 34 so as to protrude into the closed hollow space 30. In other words, the tapered portion 340 overhangs inward (i.e., toward the closed hollow space 30) from the adhesive layer 34. The thickness t1 of the adhesive layer 34 is within a range from 20 µm to 40 µm. The protruding length (i.e., an overhang) L1 of the tapered portion 340 is equal to or larger than 2.5 t1.

In the condition of the green laminate body, the thickness t0 of the green adhesive layer 349 is within a range from 40 µm to 80 µm. The protruding length (i.e., overhang) L0 of the tapered portion 340 is equal to or larger than 2 t0.

In general, the green adhesive layer 349 shrinks during the manufacturing processes of the gas sensing element 3. However, the arrangement of the second embodiment can suppress the tensile stress acting between the solid electrolytic layer 33 and the support 35 (which serve as the first and second ceramic green sheets). This is effective to eliminate the peeling-off phenomenon of the ceramic sheets and also to suppress the generation of cracks.

As apparent from the above first and second embodiments, the present invention provides a first ceramic laminate body (1; 3) comprising the first ceramic sheet (11, 115; 33) and the second ceramic sheet (12; 35) which are bonded via the adhesive layer (13, 135; 34) so as to form the closed hollow space (10; 30) between the first ceramic sheet and the second ceramic sheet. The tapered portion (130; 340) with a slant surface is formed at the inner end of the adhesive layer so as to protrude into the closed hollow space. The thickness t1 of the adhesive layer is equal to or smaller than 40 μm. And, a protruding length L1 of the tapered portion (130; 340) is equal to or larger than 2.5 t1.

If the thickness t1 exceeds 40 μm, the first and second ceramic sheets will be subjected to a large tensile stress causing due to contraction during the sintering operation, possibly causing the cracks.

If the protruding length L1 is shorter than 2.5 t, the effect of providing the tapered portion will be significantly decreased.

To obtain excellent properties, it is preferable to set an upper limit of L1 equivalent to 4 t1.

Enlarging the protruding length L1 will reduce an angle A1 formed between the inclined surface of the tapered portion and the side wall of the closed hollow space as shown in FIG. 1C. In other words, the angle A1 approaches 90 degrees. This is not preferable in eliminating generation of cracks because a large stress tends to concentrate on the corner of A1=nearly 90° when the ceramic laminate body is subjected to a thermal stress.

The ceramic laminate body of the present invention can be applied to various gas sensing elements, such as oxygen sensors, NOx sensors, and $CO_2$ sensors, which are usually an electromotive force type or limit-current type. In this case, the electrodes are provided on the surfaces of the first and second ceramic sheets. The closed hollow space is used to store a reference gas (e.g., air) or a measured gas (refer to the second embodiment).

The number of first and second ceramic sheets is not limited and therefore can be flexibly changed.

Preferably, the thickness t1 of the adhesive layer is in a range from 20 μm to 40 μm.

If the thickness t1 is less than 20 μm, the angle A1 approaches 90 degrees, and will cause the cracks when the ceramic laminate body is subjected to a thermal stress.

If the thickness t1 exceeds 40 μm, the green adhesive layer will contract greatly and cause a large tensile stress, possibly causing the cracks in the first and second ceramic sheets.

Furthermore, the present invention provides a first method for manufacturing a ceramic laminate body, comprising a step of forming a green laminate body by laminating the first ceramic green sheet (21, 215) and the second ceramic green sheet (22) via the green adhesive layer (23, 235) so as to form the closed hollow space (20) between the first and second ceramic green sheets, and a step of sintering the green laminate body. The tapered portion (230) with a slant surface is formed at the inner end of the green adhesive layer so as to protrude into the closed hollow space. The thickness t0 of the green adhesive layer is within the range from 40 μm to 80 μm. The protruding length L0 of the tapered portion (230) is equal to or larger than 2 t0.

If the thickness t0 of the green adhesive layer is less than 40 μm, the bonding strength between the first and second ceramic green sheets will be decreased. During the sintering operation, voids possibly generate and the ceramic sheets may peel off the adhesive layer.

If the thickness t0 of the green adhesive layer exceeds 80 μm, the green adhesive layer will contract greatly and cause a large tensile stress, possibly causing the cracks in the first and second ceramic sheets.

If the protruding length L0 is shorter than 2 t0, the effect of providing the tapered portion will be significantly decreased.

To obtain excellent properties, it is preferable to set an upper limit of L0 equivalent to 4 t0.

Third Embodiment

Figure 7:
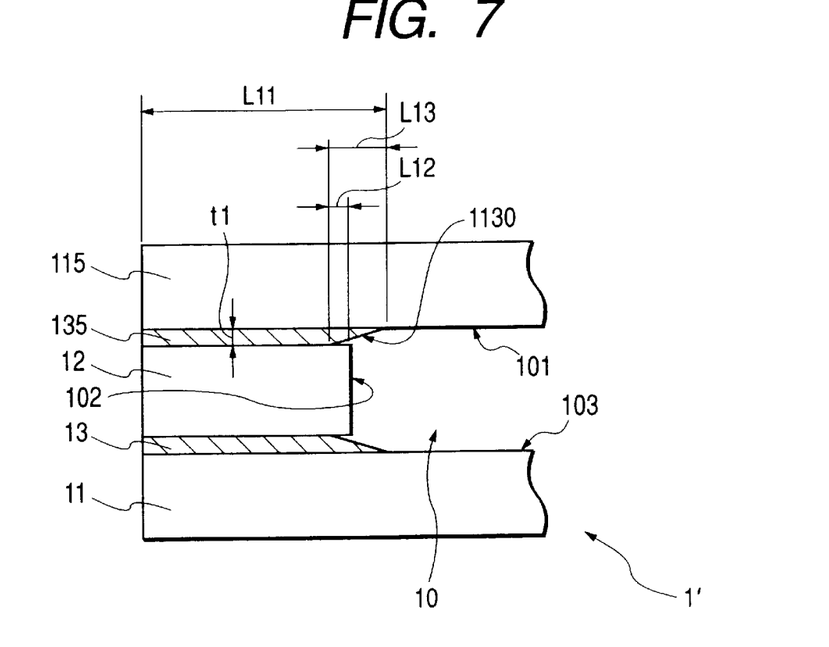
FIG. 7 is a cross-sectional view showing a ceramic laminate body in accordance with a third embodiment of the present invention.
Figure 8:
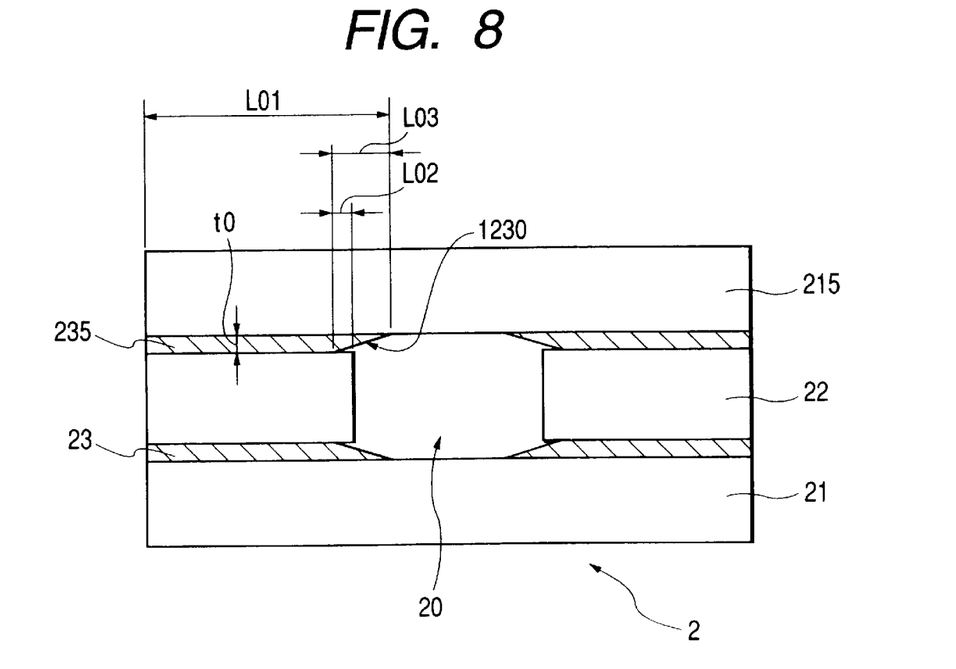
FIG. 8 is a cross-sectional view showing a green laminate body in accordance with the third embodiment of the present invention.
Figure 9:
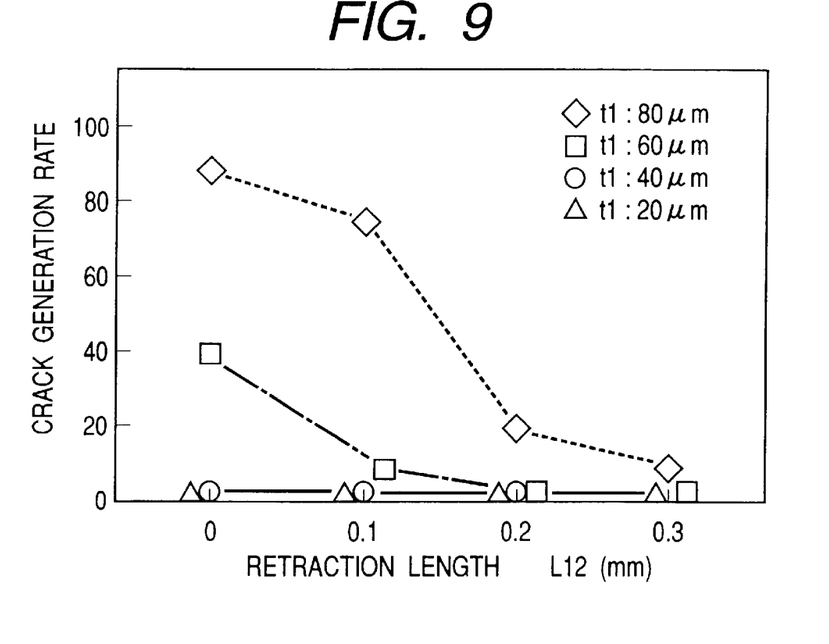
FIG. 9 is a graph showing the relationship between a retraction length L12 and the crack generation rate at several values of the thickness t1 in accordance with the third embodiment of the present invention.

FIGS. 7 to 9 show a ceramic laminate body of the third embodiment which is characteristic in the structure of the tapered portion with a slant surface which retracts at its proximal end in the gap for the adhesive layer and protrudes at its distal end into the closed hollow space.

As shown in FIG. 7, the ceramic laminate body 1' of the third embodiment comprises a lower ceramic sheet 11 (serving as a first ceramic sheet) made of alumina, an intermediate ceramic sheet 12 (serving as a second ceramic sheet) made of alumina and mounted on the lower ceramic sheet 11 via an adhesive layer 13, and an upper ceramic sheet 115 (serving as another first ceramic sheet) made of zirconia and mounted on the intermediate ceramic sheet 12 via an adhesive layer 135. A closed hollow space 10, surrounded by the upper and lower ceramic sheets 11, 115 and the intermediate ceramic sheet 12, is formed in the ceramic laminate body 1'.

A tapered portion 1130 with a slant surface, formed at an inner end of each of the adhesive layers 13 and 135, protrudes into the hollow space 10 from an inner end of the intermediate ceramic sheet 12 (i.e., from the side wall 102 of the closed hollow space 10).

A proximal end of the tapered portion 1130 (i.e., a starting point of the slant surface) retracts in the gap for the adhesive layer 13 (and 135) formed between the first ceramic sheet 11 (115) and the second ceramic sheet 12. Namely, the proximal end of the tapered portion 1130 (i.e., a starting point of the slant surface) offsets outward from the corner edge of the intermediate ceramic sheet 12 where the upper (or lower) surface of intermediate ceramic sheet 12 meets with the side wall 102 of the hollow space 10. A distal end of the tapered portion 1130 (i.e., an ending point of the slant surface) merges into the inside surface of the lower ceramic sheet 11 or the upper ceramic sheet 115. The inside surface (i.e., an upper surface) of the lower ceramic sheet 11 serves as a bottom 103 of the closed hollow space 10. The inside surface (i.e., a lower surface) of the upper ceramic sheet 115 serves as a ceiling 101 of the closed hollow space 10.

On the cross-sectional view shown in FIG. 7, the thickness t1 of the adhesive layer 13 (and 135) is 30 μm (i.e., t1=30 μm). An overall longitudinal length L11 of the adhesive layer 13 (and 135) is 1.2 mm (i.e., L11=1.2 mm). The overall longitudinal length L11 is a distance from the outer edge of the adhesive layer 13 (and 135) to the distal end of the tapered portion 1130. A retraction length L12 of the tapered portion 1130 is 0.1 mm (i.e., L12=0.1 mm). The retraction length L12 is defined as a distance from the side wall 102 to the proximal end of the tapered portion 1130. An extended length L13 of the tapered portion 1130 is longer than the retraction length L12 (i.e., L13>100 μm). The extended length L13 is defined as a longitudinal distance from the proximal end to the distal end of the tapered portion 1130.

Furthermore, the following relationship is established.

$$0 < L12 < 0.5\ L11$$

The ceramic laminate body 1' of the third embodiment is manufactured in the following manner.

As shown in FIG. 8, a second ceramic green sheet 22 is mounted on a first ceramic green sheet 21 via a green adhesive layer 23. Another first ceramic green sheet 215 is mounted on the second ceramic green sheet 22 via a green adhesive layer 235. As explained in the first embodiment, because of surface tension, the green adhesive layer 23 (235) expands naturally along its back side brought into contact with the first ceramic green sheet 21 (215) when applied thereon. Thus, the tapered portion 1230 is formed at the inner end of each of the green adhesive layers 23 and 235.

The tapered portion 1230 has an inclined surface which protrudes at its distal end into a closed hollow space 20 and retracts at its proximal end in the gap for the green adhesive layer 23 (and 235) formed between the first ceramic green sheet 21 (215) and the second ceramic green sheet 22.

The thickness t0 of the green adhesive layer 23 (and 235) is 60 μm (i.e., t0=60 μm). An overall longitudinal length L01 of the green adhesive layer 23 (and 235) is 1.5 mm (i.e., L01=1.5 mm). The overall longitudinal length L01 is a distance from the outer edge of the green adhesive layer 23 (and 235) to the distal end of the tapered portion 1230. A retraction length L02 of the tapered portion 1230 is 0.13 mm (i.e., L02=0.13 mm). The retraction length L02 is defined as a distance from the side wall 102 to the proximal end of the tapered portion 1230.

An extended length L03 of the tapered portion 1230 is longer than the retraction length L02 (i.e., L03>130 μm). The extended length L03 is defined as a longitudinal distance from the proximal end to the distal end of the tapered portion 1230. Preferably, the extended length L03 is equal to or larger than 2 t0.

Furthermore, the following relationship is established.

$$0 < L02 < 0.5\ L01$$

FIG. 9 shows test data of the ceramic laminate body 1' of the third embodiment, according to which the relationship between the retraction length L12 of the adhesive layer 13 (and 135) and the crack generation rate was obtained at several values of the thickness t1 of the adhesive layer 13 (and 135).

As understood from FIG. 9, no cracks were found in the examples having the thickness of t1=20 μm or t1=40 μm. On the other hand, a great amount of cracks were found in the examples having the thickness of t1=60 or t1=80 μm, especially when the retraction length L12 is short.

From the test result shown in FIG. 9, it is confirmed that limiting the thickness t1 within the range from 10 μm to 40 μm is effective to suppress generation of cracks.

As apparent from the foregoing description, the ceramic laminate body 1' of the third embodiment has the tapered portion 1130 with a slant surface which retracts at its proximal end in the gap for the adhesive layer 13 (and 135) formed between the first ceramic sheet 11 (115) and the second ceramic sheet 12 and protrudes at its distal end into the closed hollow space 10. The thickness t1 of the adhesive layer 13 (and 135) is within the range from 10 μm to 40 μm. The extended length L13 of the tapered portion 1130 is equal to or larger than 2.5 t1. The retraction length L12 and the overall longitudinal length L11 of the adhesive layer 13 (and 135) satisfies the following relationship.

$$0 < L12 < 0.5\ L11$$

With this arrangement, the third embodiment can suppress the tensile stress acting among the first and second ceramic sheets 11, 115, and 12 during the manufacturing processes of the ceramic laminate body 1'. This is effective to eliminate the peeling-off phenomenon of the ceramic sheets and also to suppress the generation of cracks.

Fourth Embodiment

Figure 10:
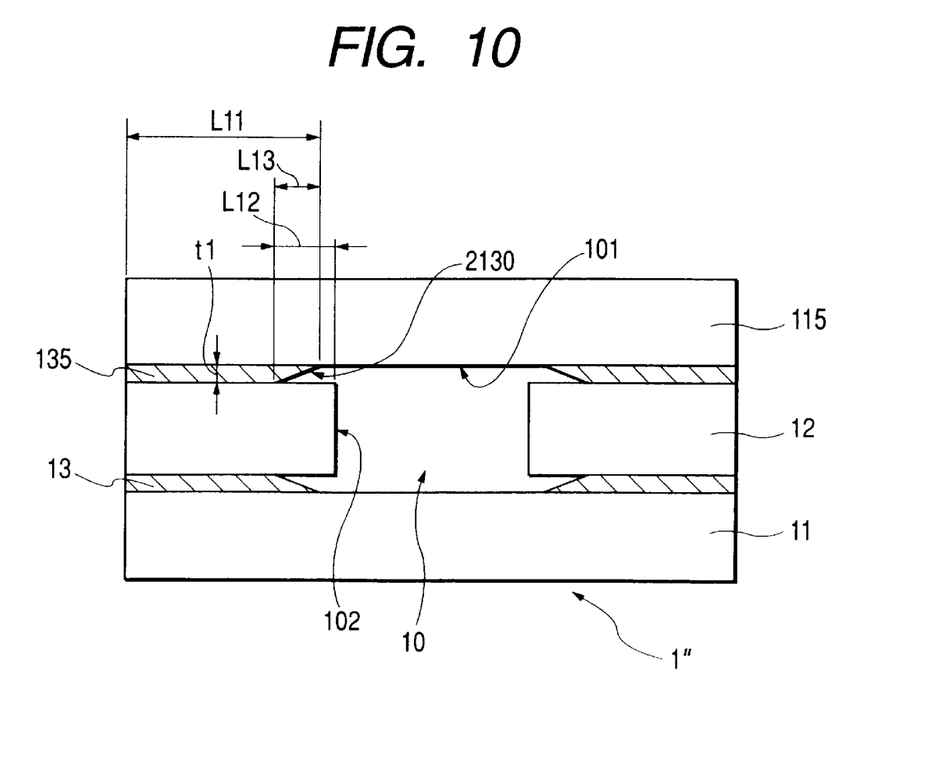
FIG. 10 is a cross-sectional view showing a ceramic laminate body in accordance with a fourth embodiment of the present invention.

FIG. 10 shows a ceramic laminate body in accordance with the fourth embodiment of the present invention, which is characteristic in that the tapered portion completely retracts in the gap for the adhesive layer.

More specifically, the ceramic laminate body 1" of the fourth embodiment has a tapered portion 2130 with a slant surface which retracts at both of its proximal end and its distal end in the gap for the adhesive layer 13 (and 135) formed between the first ceramic plate 11 (and 115) and the second ceramic plate 12.

The rest of the arrangement is identical with that disclosed in the third embodiment.

In other words, the fourth embodiment differs from the third embodiment in that the retraction length L12 is longer than the extended length L13 of the tapered portion 2130.

The thickness t1 of the adhesive layer 13 (and 135) is within the range from 10 μm to 40 μm. The extended length L13 of the tapered portion 2130 is equal to or larger than 2.5 t1. The extended length L13 is defined as a distance from the proximal end to the distal end of the tapered portion 2130. The retraction length L12 and the overall longitudinal length L11 of the adhesive layer 13 (and 135) satisfies the following relationship.

$$0 < L12 < 0.5\ L11$$

The retraction length L12 is defined as a distance from the side wall 102 of the closed hollow space 10 to the proximal end of the tapered portion 2130.

As apparent from the above third and fourth embodiments, the present invention provides a second ceramic laminate body (1', 1") comprising the first ceramic sheet (11, 115; 33) and the second ceramic sheet (12; 35) which are bonded via the adhesive layer (13, 135; 34) so as to form the closed hollow space (10; 30) between the first ceramic sheet and the second ceramic sheet. The tapered portion (1130; 2130) with a slant surface is formed the an inner end of the adhesive layer so as to retract at least partly in the gap for the adhesive layer formed between the first and second ceramic sheets. The thickness t1 of the adhesive layer is within the range from 10 μm to 40 μm. The extended length L13 of the tapered portion (1130; 2130) is equal to or larger than 2.5 t1. And, the following relationship is established:

$$0 < L12 < 0.5\ L11$$

where L11 represents the overall longitudinal length of the adhesive layer, and L12 is a retraction length of the tapered portion (1130; 2130).

If the thickness t1 is less than 10 μm, the angle A1 becomes sharp, and will cause the cracks when the ceramic laminate body is subjected to a thermal stress.

If the thickness t1 exceeds 40 μm, the green adhesive layer will contract greatly and cause a large tensile stress, possibly causing the cracks in the first and second ceramic sheets.

If the extended length L13 is shorter than 2.5 t, the effect of providing the tapered portion will be significantly decreased.

To obtain excellent properties, it is preferable to set an upper limit of L13 equivalent to 4 t1.

If the retraction length L12 exceeds 0.5 L11, the contact surface of the adhesive layer and the first (second) ceramic sheet will decrease. This will induce the peeling-off phenomenon.

Moreover, the present invention provides a second method for manufacturing the ceramic laminate body, comprising a step of forming a green laminate body by laminating the first ceramic green sheet (21, 215) and the second ceramic green sheet (22) via the green adhesive layer (23, 235) so as to form the closed hollow space (20) between the first and second ceramic green sheets, and a step of sintering the green laminate body. The tapered portion (1230) with a slant surface is formed at the inner end of the green adhesive layer so as to retract at least partly in the gap for the green adhesive layer formed between the first and second ceramic green sheets. The thickness t0 of the green adhesive layer is within the range from 20 μm to 80 μm. The extended length L03 of the tapered portion (1230) is equal to or larger than 2 t0. And, the following relationship is established:

0<L02<0.5 L01 where L01 represents the overall longitudinal length of the green adhesive layer, and L02 is the retraction length of the tapered portion (1230).

If the thickness t0 of the green adhesive layer is less than 20 μm, the bonding strength between the first and second ceramic green sheets will be decreased. During the sintering operation, voids possibly generate and the ceramic sheets may peel off the adhesive layer.

If the thickness t0 of the green adhesive layer exceeds 80 μm, the green adhesive layer will contract greatly and cause a large tensile stress, possibly causing the cracks in the first and second ceramic sheets.

If the extended length L03 is shorter than 2 t0, the effect of providing the tapered portion will be significantly decreased.

To obtain excellent properties, it is preferable to set an upper limit of L03 equivalent to 4 t0.

If the retraction length L02 exceeds 0.5 L01, the contact surface of the adhesive layer and the first (second) ceramic sheet will decrease. This will induce the peeling-off phenomenon.

Figure 11:
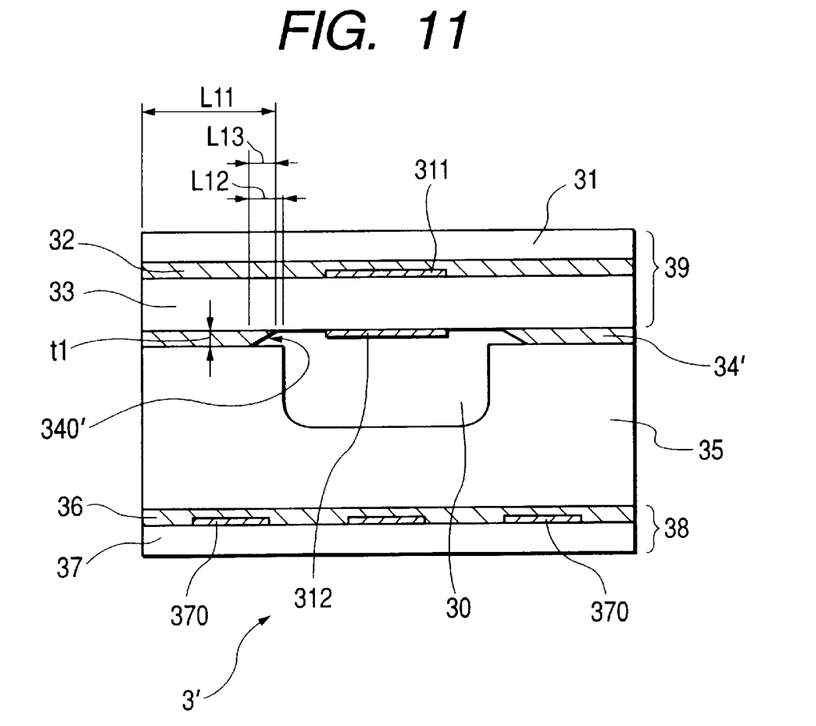
FIG. 11 is a cross-sectional view showing a gas sensing element in accordance with the fourth embodiment of the present invention.

FIG. 11 shows a gas sensing element 3' in accordance with the fourth embodiment of the present invention. The gas sensing element 3' is structurally identical with the gas sensing element 3 of the second embodiment explained with reference to FIGS. 4 to 6, except the adhesive layer interposed between the solid electrolytic layer 33 and the support 35.

Namely, the gas sensing element 3' comprises an adhesive layer 34' which bonds the lower surface of the solid electrolytic layer 33 to the upper surface of the support 35 so as to define the closed hollow space 30.

A tapered portion 340' with a slant surface is formed at an inner end of the adhesive layer 34' so as to retract at least partly in a gap for the adhesive layer 34' formed between the gas sensor section 39 (i.e., solid electrolytic layer 33) and the support 35.

The adhesive layer 34' of the gas sensing element 3' completely retracts in the gas in accordance with the fourth embodiment of the present invention. However, the adhesive layer 34' of the gas sensing element 3' can be modified to comply with the third embodiment of the present invention, by forming the inner end of the adhesive layer 34' so as to protrude into the closed hollow space 30.

The thickness t1 of the adhesive layer 34' is within a range from 10 μm to 40 μm. The extended length L13 of the tapered portion 340' is equal to or larger than 2.5 t1, and the following relationship is established:

0<L12<0.5 L11 where L11 represents the overall longitudinal length of the adhesive layer 34', and L12 is the retraction length of the tapered portion 340'.

An application of the present invention is not limited to a 1-cell type laminate gas sensor. For example, the present invention is applicable to a 2-cell type laminate gas sensor or other types.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A ceramic laminate body comprising a first ceramic sheet and a second ceramic sheet which are bonded via an adhesive layer so as to form a closed hollow space between said first ceramic sheet and said second ceramic sheet, wherein a tapered portion with a slant surface is formed at an inner end of said adhesive layer so as to protrude into said closed hollow space, said tapered portion has a thickness not exceeding a thickness t1 of said adhesive layer intervening between said first and second ceramic sheets, so as to prevent said tapered portion from extending along a perpendicular side surface of a neighboring ceramic sheet beyond an interface or boundary between said adhesive layer and said neighboring ceramic sheet, said thickness t1 of said adhesive layer is equal to or smaller than 40 μm, and a protruding length L1 of said tapered portion is equal to or larger than 2.5 t1.

2. The ceramic laminate body in accordance with claim 1, wherein said thickness t1 of said adhesive layer is in a range from 20 μm to 40 μm.

3. A ceramic laminate body comprising a first ceramic sheet and a second ceramic sheet which are bonded via an adhesive layer so as to form a closed hollow space between said first ceramic sheet and said second ceramic sheet, wherein a tapered portion with a slant surface is formed at an inner end of said adhesive layer so as to retract at least partly in a gap for said adhesive layer formed between said first and second ceramic sheets, a thickness t1 of said adhesive layer is within a range from 10 μm to 40 μm, an extended length L13 of said tapered portion is equal to or larger than 2.5 t1, and the following relationship is established:

0<L12<0.5 L11 where L11 represents an overall longitudinal length of said adhesive layer, and L12 is a retraction length of said tapered portion.

4. A gas sensing element comprising:

a sensor section for measuring a gas concentration of a measured gas; and a support for supporting said sensor section, wherein said sensor section comprises a solid electrolytic layer, and a pair of electrodes formed on opposite surfaces of said electrolytic layer;

said support has a recessed portion defining a closed hollow space when said support is assembled with said sensor section, an adhesive layer is interposed between said sensor section and said support to bond a surface of said solid electrolytic layer to a surface of said support so that said closed hollow space is formed between said solid electrolytic layer and said support, a tapered portion with a slant surface is formed at an inner end of said adhesive layer so as to protrude into said closed hollow space, said tapered portion has a thickness not exceeding a thickness t1 of said adhesive layer intervening between said solid electrolytic layer and said support, so as to prevent said tapered portion from extending along a perpendicular side surface of said support beyond an interface or boundary between said adhesive layer of said support, said thickness t1 of said adhesive layer is equal to or smaller than 40 µm, and a protruding length L1 of said tapered portion is equal to or larger than 2.5 t1.

5. A gas sensing element comprising:

a sensor section for measuring a gas concentration of a measured gas; and a support for supporting said sensor section, wherein said sensor section comprises a solid electrolytic layer, and a pair of electrodes formed on opposite surfaces of said solid electrolytic layer, said support has a recessed portion defining a closed hollow space when said support is assembled with said sensor section, an adhesive layer is interposed between said sensor section and said support to bond a surface of said solid electrolytic layer to a surface of said support so that said closed hollow space is formed between said solid electrolytic layer and said support, a tapered portion with a slant surface is formed at an inner end of said adhesive layer so as to retract at least partly in a gap for said adhesive layer formed between said sensor section and said support, a thickness t1 of said adhesive layer is within a range from 10 µm to 40 µm, an extended length L13 of said tapered portion is equal to or larger than 2.5 t1, and the following relationship is established:

0<L12<0.5 L11 where L11 represents an overall longitudinal length of said adhesive layer, and L12 is a retraction length of said tapered portion.

6. A laminated ceramic gas sensing device comprising at least two laminated sheets of substantially identical ceramic material, one of said sheets having an included aperture with an adhesive layer of thickness t1 disposed thereabout and bonding it to another of said layers, said adhesive layer including a tapered inner edge protruding into said aperture, said tapered inner edge having a width L1 and a thickness not exceeding the thickness t1 of said adhesive layer intervening between said at least two laminated sheets, so as to prevent said tapered inner edge from extending along a perpendicular side surface of a neighboring sheet beyond an interface or boundary between said adhesive layer and said neighboring sheet, wherein L1 is equal to or larger than 2.5 t1.

7. A laminated ceramic gas sensing device as in claim 6 wherein 20 µm<t1<40 µm.

8. A laminated ceramic gas sensing device as in claim 6 wherein said tapered edge protrudes into said aperture by its entire width L1.

9. A laminated ceramic gas sensing device comprising at least two laminated sheets of substantially identical ceramic material, one of said sheets having an included aperture with an adhesive layer of thickness t1 disposed thereabout and bonding it to another of said layers, said adhesive layer including a tapered inner edge protruding into said aperture, said tapered edge having a width L1, wherein L1≧2.5 t1; and said tapered edge protruding into said aperture by only part of its width L1, the tapered edge being retracted at least partially into a gap for said adhesive layer formed between said sheets of ceramic material such that

0<L12<0.5 L11 where L11 represents the overall width of said adhesive layer and L12 is the width of the tapered edge portion that is retracted into said gap.

* * * * *